United States Patent

Skeen et al.

Patent Number: 5,273,528
Date of Patent: Dec. 28, 1993

[54] LIVESTOCK INOCULATOR

[76] Inventors: Mikell L. Skeen, P.O. Box 67, Picacho, N. Mex. 88343; Sam L. Shackelford, P.O. Drawer H, Roswell, N. Mex. 88202

[21] Appl. No.: 911,486

[22] Filed: Jul. 10, 1992

[51] Int. Cl.[5] .............................. A61B 17/20
[52] U.S. Cl. ............................ 604/47; 604/46; 604/310; 606/131; 401/195
[58] Field of Search ............... 604/46, 47, 289, 290, 604/309, 310; 606/116, 131; 15/111; 81/9.22; 401/123, 124, 195

[56] References Cited

U.S. PATENT DOCUMENTS

| 301,439 | 7/1884 | Ely | 401/195 |
|---|---|---|---|
| 652,999 | 7/1900 | Denis . | |
| 866,995 | 9/1907 | Wright | 604/47 |
| 1,089,019 | 3/1914 | Swasey | 606/131 |
| 1,438,057 | 12/1922 | Pittenger | 604/47 |
| 1,467,231 | 9/1923 | Cox | 604/47 |
| 2,472,667 | 6/1949 | Lessard | 401/195 |
| 2,483,750 | 10/1949 | Bratrud | 401/195 |
| 2,541,459 | 2/1951 | Bernard | 604/289 |
| 2,818,070 | 12/1957 | Barry . | |
| 2,818,071 | 12/1957 | Barry . | |
| 2,864,370 | 12/1958 | Alvos | 604/47 |
| 2,924,219 | 2/1960 | Wershaw | 604/47 |
| 3,688,450 | 9/1972 | Brockman | 401/195 |

FOREIGN PATENT DOCUMENTS

| 1265503 | 3/1972 | United Kingdom | 401/126 |
|---|---|---|---|

*Primary Examiner*—Ralph Lewis
*Attorney, Agent, or Firm*—Dowell & Dowell

[57] ABSTRACT

A scarifier and dispensing device for inoculating livestock and other animals which includes an applicator at one end thereof and a scarifying tip extending from the opposite end thereof and which has an internal chamber for retention and dispensing of medicinal fluid which chamber is in communication with the applicator so that medicinal fluid may be dispensed as the applicator end is moved in contact with a prepared area of tissue.

15 Claims, 2 Drawing Sheets

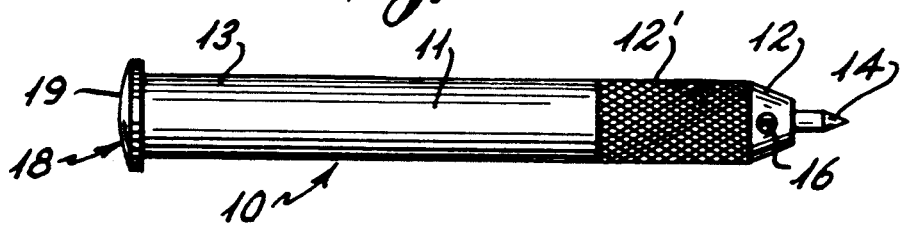
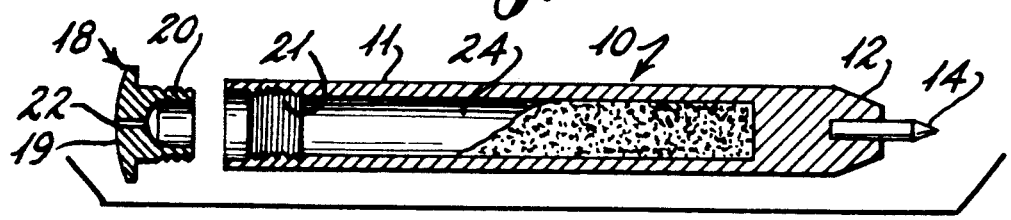
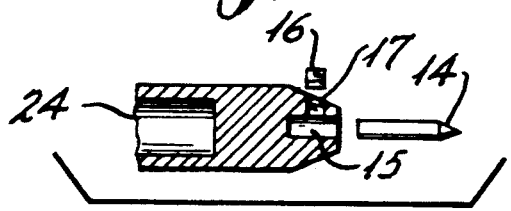
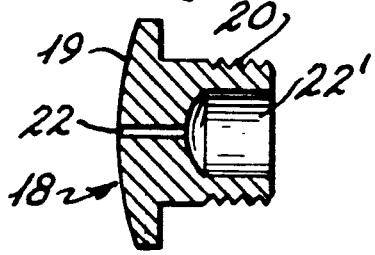
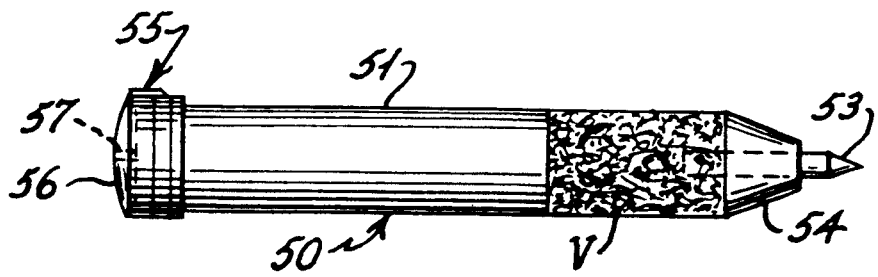

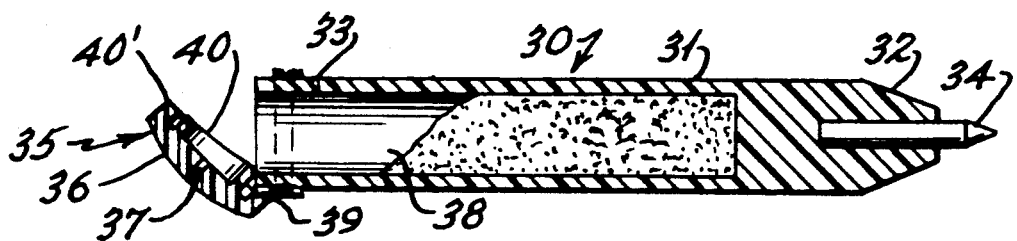
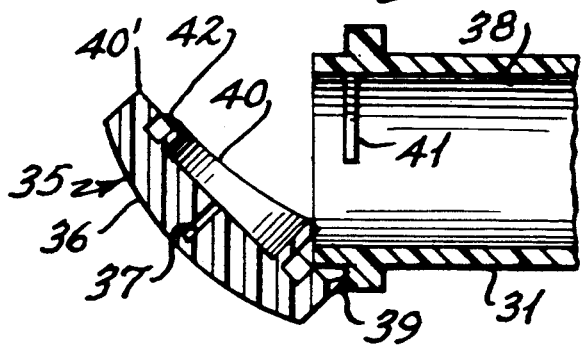
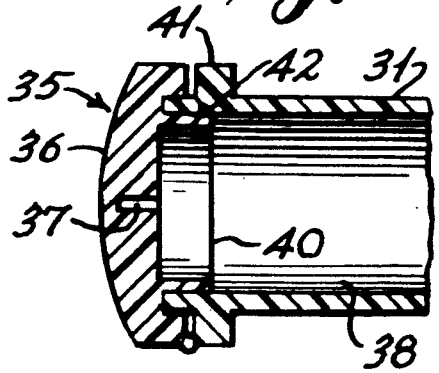
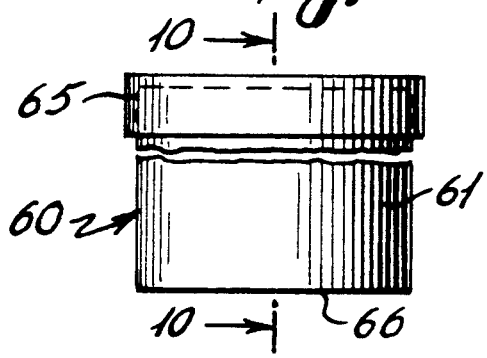
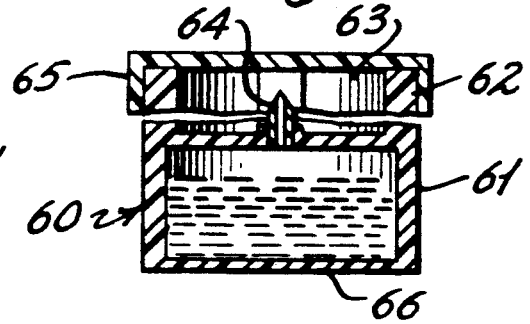
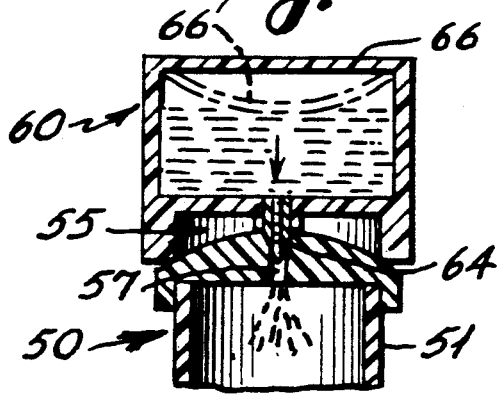
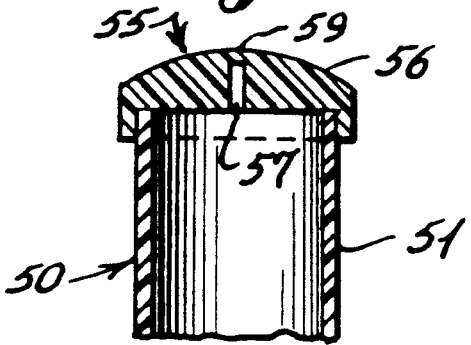

LIVESTOCK INOCULATOR

BACKGROUND OF THE INVENTION

1. Field of the Invention

This invention is generally directed to vaccinating or inoculating instruments and more specifically to scarifying applicators of the type which incorporate a pointed tip for removing the outer layer of skin of an animal to be treated and which also includes an applicator pad from which is dispensed a medicinal fluid. The present invention is also directed to such scarifying applicators which may be disposable and which may include a mixing chamber in which a dried virus is initially contained and which virus may be mixed with additional agents prior to the use of the instrument so that the inoculator serves the dual function of a medicinal container as well as an inoculating instrument. In yet another embodiment the scarifying applicator functions as a safe disposal unit.

2. History of the Related Art

In the treatment of livestock and other animals, there are often vaccines which must be applied, not by injection into the animal but by applying a virus or other vaccine to the skin of the animal. One such vaccine is utilized to treat Ovline-Ecthyma which is a disease prominent in sheep and goats. The disease affects the lips of suckling lambs and kids as well as skin areas of adults including udders and feet. The disease is transmittable to man through lesions which contact the affected area of the animal. The vaccine is distributed in a two-part packaging which includes a first container of the dried virus and a second container of a solution which is mixed with the dried virus just prior to the application of the vaccine to the animal. The rehydrating solution includes a penicillin, a fungistat as a preservative and streptomycin. The present method of applying the Ovine-Ecthyma vaccine includes utilizing a scarifying tool to remove the outer layer of skin in an area of the animal which is free from hair with the scarifying being done only to a depth sufficient to remove the outer layer and without causing bleeding. Thereafter, the mixed vaccine is applied to the scarified area after which a brush is utilized to rub the vaccine into the area. This method of applying the vaccine not only is potentially hazardous to veterinarians and other individuals working with animals being treated, as the virus can be communicated to humans, but also requires multiple handling of mixing containers, applicators and brushes to apply the vaccine to animals. Due to the complexity of application, it is frequently necessary that more than one individual handle an animal during the application of the vaccine.

Although there have been scarifying applicators proposed in the prior art, none of those proposed to date provide for the necessary utility and ease of handling and safety to assure proper vaccination of animals when applying a vaccine such as the Ovine-Ecthyma vaccine. Some examples of prior art inoculators and vaccinating instruments are disclosed in U.S. Pat. Nos. 652,999 to Denis, and 2,818,070 and 2,818,071 to Barry.

SUMMARY OF THE INVENTION

This invention is directed to scarifying inoculators for applying vaccines to livestock and other animals, and particularly to sheeps and goats, wherein the inoculators include an internal chamber or reservoir in which one or more portions of a vaccine may be packaged and thereafter mixed with other agents which activate the vaccine for application to the animals and which further include a removable scarifying tip and a pad-like applicator. The pad-like applicator which closes one end of the inoculator is in communication with the chamber of the applicator by way of a passageway extending therethrough. In some embodiments, the inoculator pad may be removably mounted to the body of the applicator so that the reservoir or chamber may be easily accessed for mixing a vaccine after which the applicator end is closed to seal the chamber. In other embodiments, one component of a vaccine may be sealed within the reservoir or chamber with any additives being injected through the passageway to the applicator pad which passageway may be initially sealed by a thin film or membrane which is severed upon the injection of a vaccine activator. As a further embodiment, the inoculator may be disposable, with the applicator pad sealing the internal chamber by locking ribs which ensure that the applicator pad, once fully seated with respect to the body portion of the inoculator, cannot be disengaged therefrom so that access to the internal chamber, after the vaccine has been placed therein, is prevented. In this manner, safe handling and disposal of the vaccine is insured.

It is a primary object of the present invention to provide an applicator and scarifying device for administrating a vaccine to animals, wherein the vaccine is safely contained within a sealed reservoir or chamber in such a manner that the vaccine cannot be spilled or splashed onto the skin of a person inoculating an animal thereby significantly decreasing the risk of infection to human beings.

It is also an object of the present invention to provide an applicator and scarifying device which also functions as a medicinal reservoir for retaining a vaccine which reservoir is in communication with an applicator surface or pad utilized to rub the vaccine into the skin of the animal being inoculated.

It is yet a further object of the present invention to provide an inoculator for applying vaccine to animals, and particularly to sheeps and goats, which includes a scarifying point which may be removed and replaced in the event that it should become damaged or dulled, or in the alternative, may be sharpened and then resecured to the body of the inoculator.

It is also an object of the present invention to provide inoculators for applying medicines to animals which allow a veterinarian or other worker to only use one hand to scarify and apply medicinal fluid from the instrument thereby allowing their other hand to be free to handle the animal during the vaccination process.

It is another object of the present invention to provide a medical scarifier and applicator which simultaneously functions as a medicinal container in which one or more portions of a vaccine may be originally contained and which also functions as a dispenser in which a vaccine is positively retained and so that accidental spillage of the vaccine which occurs with current vaccination applicators, is effectively prevented.

Another object of the present invention is to provide a disposable applicator and scarifying device wherein one or more portions of a vaccine may be originally contained and into which an activating agent may be injected so that the vaccine is mixed therein, after which, the vaccine may be dispensed therefrom.

It is another object of an alternate embodiment of the present invention to provide an inoculator which includes a mixing and dispensing reservoir or chamber which may be sealed by an integrally formed applicator cap attached to the body of the applicator and which is seated to seal the chamber in such a manner that the chamber may not be accessed once a vaccine has been introduced therein thus facilitating the handling and disposal of the vaccine.

BRIEF DESCRIPTION OF THE DRAWINGS

FIG. 1 is a side elevational view of a first embodiment of the present invention showing a scarifying tip being secured at one end of the inoculator and with an applicator pad being threaded to the opposite end thereof.

FIG. 2 is cross-sectional assembly view of the scarifying inoculator of FIG. 1.

FIG. 3 is a partial cross-sectional view of the scarifying end of the inoculator of the embodiment of FIG. 1 showing the tip being removed from the body portion thereof.

FIG. 4 is an enlarged cross-sectional view of the applicator pad of FIG. 1 showing the opening therethrough.

FIG. 5 is a cross-sectional view of a second embodiment of a scarifying inoculator of the present invention.

FIG. 6 is an enlarged partial cross-sectional view of the integrally molded applicator pad of the embodiment of FIG. 5 when initially open.

FIG. 7 is an enlarged partial cross-sectional view of the integrally molded applicator pad of FIG. 5 shown in a locked seated position relative to the body of the inoculator.

FIG. 8 is a side elevational view of a third embodiment of the present invention in the form of a disposable packaging and dispensing unit.

FIG. 9 is a front elevational view of a vaccine solution container used for activating dried virus originally packaged in the inoculator of FIG. 8

FIG. 10 is a cross-sectional view of the container of FIG. 9.

FIG. 11 is an enlarged cross-sectional view of the applicator pad of the inoculator of FIG. 8 showing the rupturable membrane that closes the opening therethrough.

FIG. 12 is a cross-sectional illustrational view showing the introduction of the activator liquid from the container of FIG. 9 into the inoculator of FIG. 8.

DESCRIPTION OF THE PREFERRED EMBODIMENT

With continued reference to the drawing figures and specifically FIGS. 1-4 a first embodiment of the present invention is shown in detail. In this embodiment, the inoculator 10 includes a body 11 having a front portion 12 and rear portion 13. The surface of the instrument adjacent the front portion 12 may be roughened or knurled to facilitate handling as shown at 12'. A scarifying tip 14 is selectively inserted within a channel 15 provided in the front end portion 12 of the instrument and is secured therein by a set screw 16 which extends through an opening 17 and into engagement with the shank of the scarifying tip. Generally, the tip is made of a metallic material which may be selectively replaced or removed from the instrument for sharpening, after which, it may be re-inserted and the set screw engaged therewith to lock the tip into seated position within the instrument. The scarifying tip resembles the tip of a nail, as opposed to the tip of a needle, as it is only utilized to penetrate or remove the outer layer of skin of an animal without penetrating the inner layers so that no blood is drawn during scarifying.

In the present embodiment, the rear portion 13 of the instrument is selectively closed by an applicator cap 18 which includes an outer slightly convex pad surface 19 which is utilized to massage or work into the animal's skin a vaccine which has been applied and which further includes an inwardly directed skirt 20 which is threaded so as to engage screw threads 21 provided in the interior of the end portion 13 of the instrument. A small orifice or opening 22 is provided through the applicator cap so as to communicate the applicator pad surface 19 with a reservoir or chamber 24 formed interiorly of the instrument by way of a tapered recessed area 22', as is shown in FIG. 2. The recess 22' tapers inwardly from the chamber toward the pad surface to facilitate the dispensing of vaccine from the chamber.

In the embodiment shown in FIGS. 1-4, the body of the instrument is preferably made of either a metal or plastic material with the applicator pad being formed of the same material. The scarifying point is preferably formed of metal which may be re-sharpened when necessary. In some embodiments the scarifying tip could be made of a hardened plastic material which would be replaced when necessary.

In the use of the embodiment of invention shown in FIGS. 1-4, a vaccine is introduced into the reservoir or chamber 24 and thereafter the applicator cap 18 is secured to seal the chamber. It should be noted that as opposed to using screw threads as shown in drawing FIG. 2, the applicator pad could be snap-fitted or friction-fitted within the rear portion of the instrument. In the use of vaccines such as Ovine-Ecthyma which include a virus which must be mixed with liquid activators just prior to administering the vaccine, the reservoir or chamber 24 serves as a mixing chamber in which the dried virus portion of the vaccine is placed and thereafter the activator added. After the liquid activator has been added, the applicator cap is secured to the rear portion of the instrument and the instrument vigorously shaken to ensure complete mixing of the vaccine therein. When using the inoculator of FIGS. 1-4 to treat an animal, a small surface area of the animal where there is little hair is scarified utilizing the tip 14 of the instrument. Thereafter, the instrument is simply rotated in the user's hand and a minor amount of the vaccine allowed to pass through the opening 22 in the cap 18. This vaccine is applied directly to the scarified area as the applicator pad surface 19 is rubbed against the skin to promote the penetration of the vaccine. Because of the tapered recessed area 22' within the applicator cap 18, vaccine is drawn from the chamber 24 by a capillary action through opening 22. Regulating the diameter of the opening 22 and configuration of the recessed area of the cap will adjust the dispensing rate of the instrument. After the instrument has been used, if it is made of a metallic material, it may be readily prepared for subsequent use by sterilization. During sterilization the applicator cap 18 should be removed to allow the chamber 24 to also be completely sterilized.

With respect to FIGS. 5-7, a second embodiment of the present invention is disclosed in greater detail. In this embodiment, the scarifying inoculator 30 includes a body portion 31 having a front end portion 32 and a rear end portion 33. Unlike the inoculator shown in FIGS. 1-4, the inoculator shown in FIGS. 5-7 is designed to be disposable and is therefore formed of a relatively inexpensive plastic material. In this respect, the scarifying tip 34 may be permanently secured to the front end of the instrument and may be formed of either a metal or plastic material. As with the previous embodiment, an applicator cap 35 is provided having an outer generally convex surface area which forms a pad 36 for facilitating the application of a vaccine to a scarified surface area. A small opening 37 is made through the cap and allows the cap to communicate with an interior reservoir or chamber 38 formed within the body 31 With this embodiment, the applicator cap 35 is formed integrally with the body portion 31 and is attached thereto by a living hinge 39. The applicator cap is designed to be securely seated and locked in engagement with the rear portion 33 of the instrument after the vaccine has been placed within chamber 38 in such a manner that the cap may not be opened without the use of extreme force being applied thereto, so that once the inoculator has been used, it may be dispensed of while safely enclosing any unused portion of the vaccine therein. In some instances, a small drop of adhesive may be placed in the opening 37 to seal the opening. In this respect, the cap 35 includes inner and outer annular skirts 40 and 40' which are of a size to frictionally engage on opposite sides of the annular wall defining the rear body portion opening into the chamber 38. A semi-circular ratchet-like flange 41 is integrally molded within the body chamber and functions to engage a mating semi-circular ratchet-like flange 42 formed on and extending outwardly from the inner skirt 39. Thus, after a vaccine has been placed within the chamber 38, the cap is closed relative to the end portion 33 of the instrument until the ratchet segment 42 passes beyond the inter-engaging ratchet segment 41, thereby locking the cap into sealed engagement with the instrument body. The cap cannot be re-opened without substantially destroying the body of the inoculator and thus the vaccine is safely retained therein. Once the cap 35 has been closed, the inoculator 30 is used to apply vaccine in the same manner as discussed with respect to the initial embodiment.

A further embodiment of the present invention is disclosed in FIGS. 8–11. In this embodiment, the applicator 50 serves a dual function as a supply container, as well as a scarifying inoculator. As with the embodiment shown in FIGS. 5–7, this embodiment of the invention is designed to be disposable but is also designed to reduce the cost of handling and dispensing of vaccines by eliminating the need to separately package one component of a vaccine which must be activated prior to use. In this respect, the body 51 of the inoculator 50 includes a central reservoir or chamber 52 in which a dried virus V is originally packaged for shipment to a consumer. As with the previous embodiments, the instrument includes a scarifying tip 53 which extends from front end 54 of the body 51 and a rear applicator cap 55 having an outer convex surface 56 which functions as the rubbing pad for the inoculator. An opening 57 is disposed through the applicator cap 55 so as to communicate pad 56 with central chamber 52. The instrument is designed so that the applicator cap may be heat sealed or otherwise secured to the rear end portion 58 of the housing 51 after the dried virus has been inserted therein. The opening 57 is initially closed by a membrane 59 or seal extending across the outermost portion thereof. In order to activate the virus V for use, it only becomes necessary to inject the liquid activator through the opening 57 after puncturing the membrane 59 and thereafter shaking the contents of the inoculator to mix the virus with the activator.

To reduce spillage and the chance of contamination or infection of individuals handling the inoculator of the present invention, in the present embodiment, a special dispensing package 60 for the activator portion of the vaccine is shown. The package may include a body portion 61 having an upper annular flange 62 defining a recessed area 63 into which extends a small dispensing needle 64 by way of which the activator is discharged from the container. The upper end of the container defined by the flange 62 is normally sealed by a cap 65 which is removed just prior to dispensing the activator into the body of the inoculator.

As specifically shown in FIG. 11, once the cap 65 has been removed from the container 60, the applicator cap end 55 of the inoculator is seated within the recessed area 63 thereof. During this process, the dispensing needle 63 will penetrate through the membrane or seal 59 covering the outer surface thereof and thereby communicate the needle with the chamber 52 by way of the opening 57. The liquid activator is thereafter urged from container 60 by collapsing the bottom wall 66 thereof, as is shown in dotted line. Once the activator has been injected, the cap 65 may be re-attached to the container so as to prevent accidental contact with the dispensing needle 64. With this instrument, the amount of packaging required is reduced and the safe disposal of any remaining contents by retaining the contents of the vaccine within a generally sealed inoculator is achieved. The vaccine within the inoculator is applied in a manner similar to that discussed with respect to the previous embodiments.

We claim:

1. A scarifying and dispensing device for inoculating livestock and other animals with a vaccine after their skin has been scarified, comprising: a body having front and rear portions, a chamber defined internally of said body and located rearward from said front portion in which a vaccine may be selectively inserted and retained, a scarifying tip means mounted from and extending outwardly of said front portion of said body for use in removing an outer layer of skin of the animal to form a scarified surface, a substantially rigid applicator cap means closing said rear portion of said body, said applicator cap means having inner and outer surfaces, said outer surface defining a substantially continuous and smooth pad for use in rubbing vaccine into the scarified surface of the animal, and an opening of a predetermined size defined between said inner and outer surfaces of said applicator cap means for communicating said chamber with said outer surface of said applicator cap means.

2. The scarifying and dispensing device of claim 1 including a channel formed within said front portion of said body and spaced from said chamber, said scarifying tip means being removably mounted within said channel, and means for securing said scarifying tip within said channel.

3. The scarifying and dispensing device of claim 2 in which said outer surface of said applicator cap means is generally convex in configuration.

4. The scarifying and dispensing device of claim 1 in which said applicator cap means includes a generally annular skirt portion for engaging said rear portion of said body, and a recess formed within said skirt portion, said recess tapering inwardly toward said opening in said applicator cap means.

5. The scarifying and dispensing device of claim 1 including means for securely seating said applicator cap means with respect to said body after a vaccine has been placed within said chamber.

6. The scarifying and dispensing device of claim 5 in which said applicator cap means is connected to said body by a hinge means, a first locking means carried by said body and a second locking means carried by said applicator cap means, said first and second locking means being interengageable with respect to one another upon the seated closure of said applicator cap means relative to said rear portion of said body.

7. The scarifying and dispensing device of claim 6 in which said first and second locking means are integrally formed as opposing ratchet members.

8. The scarifying and dispensing device of claim 7 in which said hinge means is integrally formed with said body and said applicator cap means.

9. The scarifying and dispensing device of claim 7 including means for removably mounting said scarifying tip means to said front portion of said body.

10. The scarifying and dispensing device of claim 1 including means for initially closing said opening through said applicator cap means.

11. The scarifying and dispensing device of claim 10 including a container housing at least a portion of the vaccine to be introduced into said chamber, means for puncturing said means for initially closing said opening in said applicator cap means, said means for puncturing including a dispensing needle mounted to and extending from said container, and said dispensing needle being of a size to be receivable within said opening so as to communicate said container with said chamber.

12. A combination scarifying and dispensing system for inoculating animals by initially scarifying a portion of the skin of the animal and thereafter applying a vaccine thereto, comprising: an inoculator having a body with front and rear ends, a chamber defined within said body and located rearward from said front end, a scarifying tip extending from said front end of said body, an applicator cap closing said rear end of said body, said applicator cap having an outer surface, a first portion of said vaccine being sealed within said chamber, a container having a second portion of said vaccine contained therein, said container having a dispensing tip extending therefrom, an opening extending at least partially through said applicator cap for selectively communicating said chamber with said outer surface of said applicator cap, means for closing said opening in said applicator cap, said dispensing tip being extendable through said means for closing said opening to thereby allow said second portion of said vaccine to be introduced through said applicator cap and into said chamber to thereby allow said second portion to be mixed with said first portion of said vaccine within said chamber.

13. A scarifying and dispensing device for inoculating animals comprising an inoculator body having front and rear ends, a scarifying tip means extending outwardly from said front end of said body for use in removing an outer layer of skin of the animal to form a scarified surface and a substantially rigid applicator cap closing said rear end of said body, a chamber defined within said body, said applicator cap having a substantially dome shaped outer surface forming a pad, an opening extending through said applicator cap communicating said chamber with said dome shaped outer surface thereof.

14. The sacrifying and dispensing device of claim 13 including means for removably mounting said scarifying tip means to said front end of said body.

15. The scarifying and dispensing device of claim 13 including means for initially closing said opening through said applicator cap means.

* * * * *